US006451357B1

(12) United States Patent
Farrow

(10) Patent No.: US 6,451,357 B1
(45) Date of Patent: Sep. 17, 2002

(54) METHOD FOR PURIFICATION OF ALOESIN

(75) Inventor: Thomas M. Farrow, Denver, CO (US)

(73) Assignee: Unigen Pharmaceuticals, Inc., Broomfield, CO (US)

( * ) Notice: Subject to any disclaimer, the term of this patent is extended or adjusted under 35 U.S.C. 154(b) by 39 days.

(21) Appl. No.: 09/792,104

(22) Filed: Feb. 26, 2001

(51) Int. Cl.$^7$ .............................................. A61K 35/78
(52) U.S. Cl. ........................ 424/744; 536/1.1; 536/4.1
(58) Field of Search ................................ 536/1.11, 4.1; 514/53, 54; 424/47, 744

(56) References Cited

U.S. PATENT DOCUMENTS

| | | | |
|---|---|---|---|
| 4,656,029 A | * 4/1987 | Grollier et al. | ................ 424/47 |
| 5,801,256 A | 9/1998 | Padmapriya et al. | |
| 6,083,976 A | 7/2000 | Padmapriya et al. | |
| 6,123,959 A | 9/2000 | Jones et al. | |

FOREIGN PATENT DOCUMENTS

WO     WO 96/40182     12/1996

OTHER PUBLICATIONS

Conner et al. (1990) Phytochemistry 29:941–944.
Gramatica et al. (1982) Tetrahedron Letters 23:2423–2424.
Grindlay and Reynolds (1986) J. of Ethnopharmacology 16:117–151.
Hart et al. (1988) J. of Ethnopharmacology 23:61–71.
Haynes et al. (1970) J. Chem. Soc. (C) 2581–2586.
Hirata and Suga (1977) Z. Naturforsch 32c:731–734.
Holdsworth (1972) *Chromones in Aloe Species, Part I–Aloesin* PM 19(4):322–325.
Makino et al. (1974) Chem. Pharm. Bull 22:1565–1570.
McCarthy and Haynes (1967) *The Distribution of Aloesin in Some South African Aloe Species*; Heft 3 342–344.
Mebe (1987) Phytochemistry 26:2646–2647.
Rauwald and Beil (1993) J. of Chromatography 639:359–362.
Rauwald and Beil (1993) Z. Naturforsch 48c:1–4.
Speranza et al. (1986) Phytochemistry 25:2219–2222.
Speranza et al. (1988) J. Natural Products 51:588–590.
Speranza et al. (1985) Phytochemistry 24:1571–1573.
van Wyk et al. (1995) Planta Med. 61:250–253.
Yagi et al. (1987) Plant Medica 515–517.

* cited by examiner

Primary Examiner—James O Wilson
Assistant Examiner—Ganapathy Krishnan
(74) Attorney, Agent, or Firm—Swanson & Bratschun, L.L.C.

(57) ABSTRACT

The present invention relates generally to a method for the purification of aloesin, a C-glucosylated 5-methylchromone, tyrosinase inhibitor isolated from Aloe. Specifically, the present invention relates to a method for the crystallization of aloesin, that produces highly pure, relatively colorless aloesin

24 Claims, 1 Drawing Sheet

1. Aloesin is concentrated by ultrafiltration or reverse osmosis to > 126 mg/ml.
2. Optionally cool to 4°C, stirring.
3. Filter, rinse with cold solvent until color is removed. Washed crystals contain ~ 30% water residue.
4. Air dry crystals for 5-10 minutes residue; followed by freeze-drying.

METHOD FOR PURIFICATION OF ALOESIN

FIELD OF INVENTION

The present invention relates generally to a method for the purification of a tyrosinase inhibitor isolated from Aloe. Specifically, the present invention relates to a method for the purification of aloesin, a C-glucosylated 5-methylchromone.

BACKGROUND OF THE INVENTION

There is a world-wide demand for products able to inhibit or prevent excessive pigmentation of the skin. Melanin, the skin's natural pigment, is synthesized in the melanocytes in varying concentrations, depending on skin type (genetic disposition) and environmental effects. Melanocytes are cells which occur in the basal membrane of the epidermis, and account for between 5% and 10% of the cellular content (approximately 1200–1500 melanocytes per $cm^2$). Melanocytes are stimulated by ultraviolet (UV) light, producing greater quantities of melanin. The melanin is then transported into the keratinocytes, where it becomes visible as skin color.

The number of melanocytes in human skin is more or less the same, irrespective of skin color. The color of the skin is largely dependent on the quantity and type of melanin produced (black eumelanin or yellow to reddish-brown pheomelanin). Asians and light-skinned people have lower levels of eumelanin than dark-skinned people, and correspondingly less protection against the effects of radiation. People with red hair are characterized by pigmentation with pheomelanin, and have little or no photo-protection. Additionally, the distribution of melanin in the skin also varies. In people with light skin, the greater part of the pigment lies in the basal layer, whereas in those with dark skin, the melanin is spread throughout, reaching into the horny layer.

Tyrosinase is the key enzyme in the synthesis of melanin. It has been determined that tyrosinase needs both the substrate and divalent metal ions for its catalytic activity. The processes presently used for inhibiting the synthesis of melanin with a view to lightening skin are based on substances which interact directly with the tyrosinase, or indirectly regulate its activity, e.g., by complexing the necessary metal ions.

To date, the best-known active substance for de-pigmentation is hydroquinone, a bleaching agent. Hydroquinone, however, does not inhibit melanin biosynthesis, rather it bleaches existing melanin. If applied over long periods of time, hydroquinone can have serious side effects, which has led to its being permitted only in limited concentrations in some countries and to its being completely forbidden for applications in cosmetic products in other countries. Furthermore, hydroquinone leads to permanent de-pigmentation, and thus to increased photosensitivity of the skin when exposed to UV light.

Better tolerated skin lightening substances currently being used are of natural origin, e.g., arbutin (from the leaves of the common bearberry, Uvae ursi), liquorice extract (from liquorice root), ascorbic acid (vitamin C from citrus fruits) and their derivatives, as well as kojic acid (from carbohydrate solutions under the effect of certain bacteria) (see Kobayashi el al. (1995) BioSci. Biotech. Biochem. 59:1745). These substances, which are highly soluble in water, act on the tyrosinase as competitive inhibitors; however, they are unstable in some formulations, and have the disadvantage that only very small quantities penetrate the deeper skin layers and reach the melanocytes in the basal membrane. A further disadvantage of these substances is their low level of efficacy, which necessitates their being used in high concentrations. Compared to the quantity of hydroquinone used, 17 times as much ascorbic acid and over 100 times as much arbutin is required to achieve a similar effect.

Gombert describes two cosmetic products for lightening skin, both of which are produced from plants. (Gombert (1997) Cosmetics and Toiletries Manufacture Worldwide, pp.151–157). Both products contain a mixture of several competitive tyrosinase inhibitors in an aqueous solution, emulsified into creams. An in vitro enzyme test was carried out, in which it was possible to show that the substances used had an efficient inhibitory effect; however with in vivo tests, it was not until a cream with a 10% active ingredient content had been applied for at least 42 days that a demonstrable de-pigmentation of the skin occurred. In one test involving ten people using a cream with a 3% active ingredient content, proof of any positive effect at all could only be found with two people. It is specifically pointed out that, since the natural substances used in the formulation are extremely unstable, strong antioxidants must be added to the formulation. Also, if the finished formulations are stored at temperatures below 15° C., the substances can crystallize.

Lee and Kim (Cosmetics and Toiletries 110:51–56, October 1995), describe a substance isolated from the bark of the roots of the mulberry bush *Broussonetia papyrifera*, which acts as a free radical scavenger. As the formation of melanin, referred to as melanogenesis, is increased by the presence of free radicals in the skin, it can be reduced with the help of a free radical scavenger of this type. The subject of this article is not the de-pigmentation of skin, but rather the suppression of melanogenesis with the help of a free radical scavenger. Furthermore, it takes over 40 days for the described effect to occur. In this paper also, attention is drawn specifically to the instability of the active substances in the formulation.

Aloe is an intricate plant which contains many biologically active substances. (Cohen et al. in *Wound Healing/Biochemical and Clinical Aspects*, 1st ed. WB Saunders, Philadelphia (1992)). Over 300 species of Aloe are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-gastric ulcer, anti-diabetic, anti-tyrosinase activity (see, e.g., Yagi et al. (1977) Z. Naturforsch 32c: 731–734) and antioxidant activity (see, International Application Serial No. PCT/US95/07404).

Yagi et al. disclose a group of compounds isolated from Aloe, particularly aloesin and one of its derivatives, 2"-O-feruloylaloesin, which are effective inhibitors of tyrosinase. (Yagi et al. (1987) Plant Medica 515–517). Biochemical testing of the enzyme inhibition by means of the Lineweaver Burk diagram showed that 2"-feruloylaloesin was a non-competitive inhibitor of tyrosinase while aloesin is a competitive inhibitor. Aloesin is a C-glucosylated 5-methylchromone having the following chemical structure and conventional numbering:

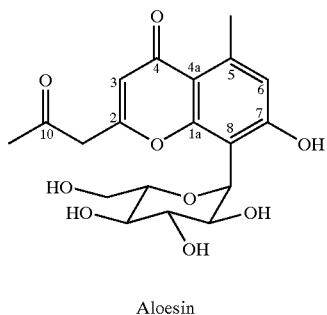

Aloesin (Holdsworth (1972) *Chromones in Aloe Species, Part I-Aloesin* PM 19(4):322–325). In vitro, aloesin is a strong inhibitor of tyrosinase activity (Yagi et al. (1987) Planta Medica 515–517). In assays of tyrosinase activity on the substrate L-DOPA, aloesin is capable of 50% inhibition at a concentration of 0.2 mM.

U.S. Pat. No. 6,083,976, entitled "Method of Synthesis of Derivatives of Aloesin." describes a novel method for the synthesis of derivatives of aloesin alkylated at the C-7 hydroxyl group. The alkylated aloesins, produced by this method have the functionality of aloesin, a tyrosinase-inhibiting compound with skin whitening activity, but have greater biological activity than aloesin as indicated by in vitro tyrosinase assays. Additionally, the alkyl group makes the derivatized aloesins more fat soluble than aloesin, allowing them to be retained in the stratum corneum of the skin more effectively than aloesin. As a result, the alkylated aloesins are more potent and faster acting skin lightening agents than aloesin.

U.S. Pat. No. 6,123,959, entitled "Aqueous Composition Comprising Active Ingredients for the De-Pigmentation of the Skin," describes aqueous compositions comprising liposomes of phospholipids, and at least one competitive inhibitor of an enzyme for the synthesis of melanin, in combination with at least one non-competitive inhibitor of an enzyme for the synthesis of melanin. The competitive inhibitors of the invention include aloesin and derivatives thereof. The invention also includes the use of the compositions for the de-pigmentation of skin. Each of these patents is incorporated herein by reference in their entirety.

To date, known methods for purifying aloesin, as well as, other chromones involve the use of chromatography. (See e.g., Rauwald and Beil (1993) J. of Chromatography 639:359–362; Rauwald and Beil (1993) Z. Naturforsch 48c:1–4; Conner et al. (1990) Phytochemistry 29:941; Holdsworth (1972) *Chromones in Aloe Species, Part I-Aloesin* PM 19(4):322–325; Mebe (1987) Phytochemistry 26:2646; Haynes et al. (1 970) J. Chem. Soc. (C) 2581; McCarthy and Haynes (1967) *The Distribution of Aloesin in Some South African Aloe Species*; Heft 3 342). These procedures were developed for chemical analysis and are not practical for preparative scale production of aloesin. Applicant knows of no report or suggestion of a method for the crystallization of aloesin or any other chromone.

SUMMARY OF THE INVENTION

The present invention includes an improved process for purifying aloesin, a C-glucosylated 5-methylchromone isolated from Aloe. Specifically, the present invention includes a method for the crystallization of aloesin, that produces highly pure, relatively colorless aloesin. In one embodiment of the invention the method comprises: reducing the volume of a partially purified solution of aloe extract containing at least 45% aloesin in an organic solvent or aqueous solution thereof, allowing the aloesin to crystallize from the solution; and isolating said crystallized aloesin. In a preferred embodiment the solution is cooled during the crystallization step. Crude aloesin produced by any method known in the art with a 45% or higher purity can be crystallized using the method of this invention.

The present invention provides a commercially viable process for the purification of aloesin. The method of the present invention provides for the manufacture of aloesin in much larger quantities and in a much more cost effective manner than currently available methods. The method of the present invention also provides for the manufacture of aloesin that has higher purity, stability and better color than currently available methods.

It is to be understood that both the foregoing general description and the following detailed description are exemplary and explanatory only and are not restrictive of the invention as claimed.

DETAILED DESCRIPTION OF THE INVENTION

Figure 1:
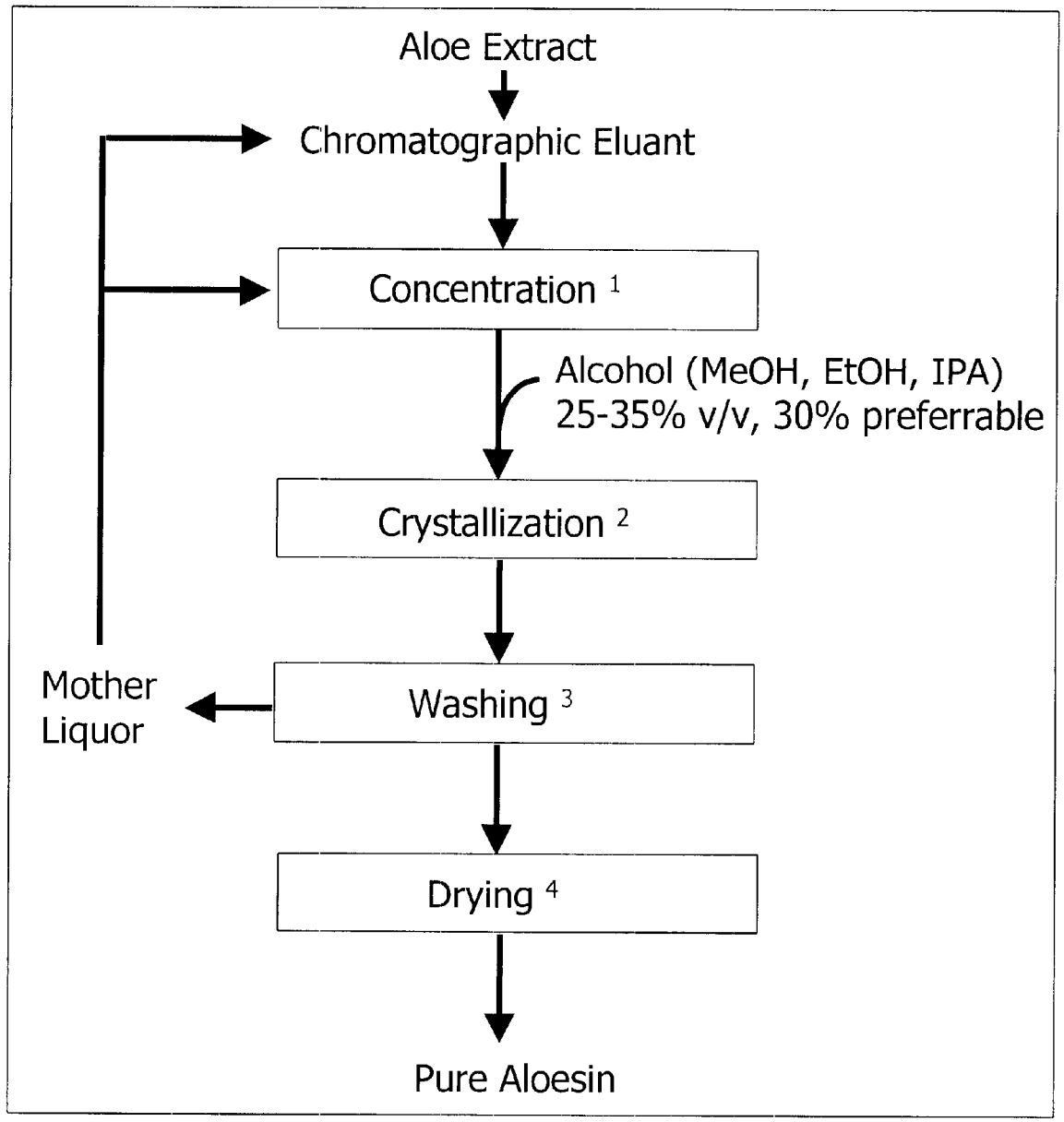
FIG. 1 illustrates schematically one embodiment of the method of this invention.

The present invention includes a method for purifying aloesin, a C-glucosylated 5-methylchromone isolated from Aloe. Specifically, the present invention includes a method for the crystallization of aloesin, that produces highly pure, relatively colorless aloesin. The general method of the invention comprises: reducing the volume of an aloe extract containing at least 45% aloesin in an organic solvent or aqueous solution thereof; allowing the aloesin to crystallize from the solution; and isolating said crystallized aloesin. In a preferred embodiment the solution is cooled during the crystallization step. Crude aloesin produced by any method known in the art with a 45% or higher purity can be crystallized using the method of this invention.

Certain terms used to describe the invention herein are defined as follows:

The term "Aloe" refers to the genus of South African plants of the Liliaceae family of which the *Aloe barbadensis* plant is a species. Aloesin is present primarily in the whole leaf of a number of different species of Aloe.

The term "Aloe extract" is defined as the dried juice of the whole leaf of various species of the Aloe plant. The "Aloe extract" used in the examples of this invention was prepared by "whole-leaf processing" of the whole leaf of various Aloe species. In one example, whole leaves obtained from the *Aloe barbadensis* plant were ground, filtered, treated with cellulase (optional) and activated carbon and lyophilized. The lyophilized powder was reconstituted with the chromatography solvent prior to use. In another example, the exudate from aloe leaves was suspended in water, followed by contact with an appropriate chromatography solvent prior to use.

The term "aloesin chromatographic eluant" as used herein refers to a partially purified solution of aloe extract containing at least 45% aloesin obtained via chromatography of aloe extract.

As used herein, the term "crystallization" is a standard term which refers to a means for purifying materials by solidification.

One embodiment of the general reaction scheme of the present invention can be illustrated as set forth in FIG. 1. With reference to FIG. 1, an Aloe extract prepared by the processing of the leaf exudate of the Aloe plant is partially purified to provide a product that contains at least a 45% or higher purity of aloesin. In a preferred embodiment, the Aloe extract is obtained from the leaf exudate of *Aloe barbadensis* or other species. The Aloe extract can be purified by any method capable of producing aloesin of this purity. In a preferred embodiment, however, the Aloe extract is purified by chromatography to produce what is referred to herein as the Aloe chromatographic eluant. One method of obtaining the Aloe chromatographic eluant using liquid chromatography (LC) is illustrated in Example 1. The Aloe chromatographic eluant used in Examples 2–5 was provided by and can be purchased from Univera Pharmaceuticals, Inc.

Following chromatography the best pool is collected and concentrated. If the aloesin is going to be crystallized from the elution solvent the chromatographic eluant is concentrated to approximately 126 mg/mL or greater. If the aloesin is going to be crystallized from a solvent other than the elution solvent then the eluant is concentrated and/or lyophilized prior to the addition of the crystallization solvent. In a preferred embodiment, the chromatographic eluant is concentrated by ultrafiltration, as exemplified in Example 3 or reverse osmosis as exemplified in Example 2.

The crystallization solvent is selected from a water miscible organic solvent, including but not limited to an alcohol, such as, methanol, ethanol or isopropanol; acetone and acetonitrile or aqueous mixtures thereof. The crystallization solvent may also be selected from a mixture of water miscible solvents, including but not limited to, a mixture of acetonitrile and an alcohol. Example 4 exemplifies the crystallization of aloesin using a mixture of acetonitrile and ethanol.

In one embodiment the crystallization solvent is selected from an alcohol or aqueous mixture thereof containing from between 0% and 100% v/v alcohol in $H_2O$. In a preferred embodiment the solution is between 25%–30% v/v alcohol/ $H_2O$, most preferably 30% alcohol in water.

Following concentration the aloesin is then allowed to crystallize. In a preferred embodiment, the crystallization mixture is cooled to approximately 4° C., for 16–20 hours with continuous stirring during the crystallization. If the crystallization solvent is an aqueous methanolic solution with a concentration of aloesin of 120 $\mu$g/mL or higher, cooling may or may not be necessary. The crystals can be collected by filtration using either vacuum or pressure. The crystals are washed with cold solvent until color is removed and are cooled to −70° C. until any water is frozen. The solids are then dried by any drying method known in the art, but preferably by lyophilization. As shown in FIG. 1 the mother liquor can then be recycled in order to obtain a higher yield of aloesin.

Example 1 describes a general method for the preparation of a partially purified solution Aloe extract used as the starting material in the method of this invention. In this Example the Aloe extract is partially purified using LC. As noted above, however, any method of purification capable of providing aloesin of at least 45% purity can be used. In Examples 2–5 the Aloe chromatographic eluant is provided by Univera Pharmaceuticals, Inc.

Example 2 illustrates the general method of this invention wherein the Aloe chromatographic eluant is concentrated by reverse osmosis. Briefly, the best pool from the Aloe chromatographic eluant is concentrated to approximately 1/10 volume using a Millipore Prolab Reverse osmosis unit or any other concentration method. This solution is cooled to about 4° C. with constant stirring for 16 hours and the crystals were collected by vacuum filtration. The crystals were washed with cold methanol/water and chilled to about −70° C. until the water was frozen. The solids were then placed into a lyophilizer until dry to yield aloesin which was 99.6% pure.

Example 3 illustrates the general method of this invention wherein the Aloe chromatographic eluant is concentrated by nanofiltration using 500 MWC filters made from cellulose acetate.

Example 4 illustrates the general method of this invention wherein the crystallization solvent is either acetonitrile or a mixture of acetonitrile in ethanol (90%/10%).

The following examples are provided for illustrative purposes only and are not intended to limit the scope of the invention.

EXAMPLES

Materials. The Aloe chromatographic eluant may be purchased from Univera Pharmaceuticals, Inc. or may be prepared by any method known in the art. One example of obtaining this eluant is via preparative High Pressure Liquid Chromatography (HPLC) as illustrated in Example 1 below. Nano Max 50 nanofilters were purchased from Millipore. Other materials used in the following Examples include a Millipore Prolab reverse osmosis unit, with two filter cartridges (4.3 sq. ft. each), Cole Parmer variable speed mixers with stainless steel blades or equivalent and Buchner vacuum filters or stainless steel pressure filters with filter paper (Whatman #1).

Example 1

Preparation of the Aloe Chromatographic Eluant

The Aloe chromatographic eluant used in the method of this invention can be obtained by any method known in the art sufficient to produce aloesin of at least about 45% purity. One method using preparative HPLC is briefly described in this Example. Aloe chromatographic eluant having this purity may also be purchased from Univera Pharmaceuticals, Inc.

The Aloe extract used in this Example was isolated from the whole leaf of *A. barbadensis* that had been previously dissolved in hot water and filtered to remove undissolved particulates. This particular run yielded 1.2 mg of aloesin that was collected as a fraction from the column eluant. With repeated runs one can collect sufficient quantities of relatively pure aloesin for crystallization.

Preparative HPLC.

Column: IB SIL C 18, 250 mm×4.6 mm, 5 $\mu$p particle size
Mobile Phase: water/methanol gradient: 80%/20% (20 minutes); 40%/60% (10 minutes); 80%/20% (10 minutes)
Temperature: Ambient Flow Rate: 1 mL/min Detector Wavelength: 297 Sensitivity: 20 Product eluted between 8–9 minutes.

Example 2

Crystallization of Aloesin in MeOH

The Aloesin chromatographic eluant used in this Example was prepared by and can be purchased from Univera Pharmaceuticals, Inc. Samples were taken and the best pool was collected and concentrated using a Millipore Prolab Reverse osmosis unit. The beginning volume was 140 L and the final volume was about 10 L. After the volume was reduced the concentrate was placed into a container and put into a cold room and stirred with a mechanical mixer for about 16 hours. The resulting crystals were collected using a polypropylene Buchner funnel with the aid of vacuum. The resulting solids (311 g) were washed with about 1 L of methanol/water (1:1). The solids were scraped out of the filter and chilled to −70° C. for about 6 hours and then lyophilized using a Vertis Genesis 25LL freeze drier. The solids were collected and analyzed.

Best pool concentrate test results:

Aloesin: 9.3 mg/mL Solids: 10.2 mg/mL 1302 grams of Aloesin present.

After crystallization:

Recovered 311 g of Aloesin at 99.61% purity with a LOD of 0.0 The x, y and z color values were: x=79.55, y=85.78, z=74.74 The bulk density was 0.345 g/mL Recovery was 23.89% from the best pool Example 3

Crystallization of Aloesin in MeOH

The Aloesin chromatographic eluant was provided by Univera Pharmaceuticals, Inc. The best pool was collected and concentrated via nanofiltration using the Millipore Prolab nanofiltration system equipped with Nano Max 50 cartridges until the volume was reduced from 135 L to about 10 L. The concentrated solution was tested and placed in a cold room, methanol as added to the solution to bring the concentration to about 30%. A mechanical stirrer was then used to mix overnight. After about 16 hours the resulting solids were filtered through Whatman #1 filter paper using a stainless steel pressure filter. The filtered solids were washed with a methanol water solution 1:1 at about 4° C. A total volume of 1 L was used to filter these solids. The solids were then chilled to −70° C. overnight and finally placed into a Vertis Genesis 25LL freeze drier until the solids were dry. The solids were removed and analyzed.

Best pool concentrate test results:

Aloesin: 85.205 mg/mL Solids: 88.73 mg/mL

After crystallization the solids were tested and the results were as follows.

790 grams solids at 100.2% pure and with a LOD of 2.17% The x, y and color values are x=81.88, y=88.67, z=73.35 The bulk density is 0.583 mg/mL Recovery is 92.72% from the best pool concentrate.

Example 4

Crystallization of Aloesin in $CH_3CN$ or $CH_3CN$/EtOH

Aloesin (300 g lyophilized chromatographic best pool concentrate) was added to boiling acetonitrile or acetonitrile 90% ethanol 10% and mixed until all particles were in solution. This solution was then filtered (hot) through Whatman #1 filter paper or equivalent and the filtrate was stirred for several hours. The crystals were then collected by filtration. Yields range from 90% to 20% with the purity of aloesin in the lower 90% range.

What is claimed is:

1. A method for the purification of aloesin comprising the steps of:
   a) reducing the volume of an aloe extract containing at least 45% pure aloesin in an organic solvent or aqueous solution thereof;
   b) allowing said aloesin to crystallize from said solution; and
   c) isolating said crystallized aloesin.

2. The method of claim 1 further comprising the step of cooling said solution of aloesin during step b).

3. The method of claim 2 wherein said solution is cooled to about 4° C.

4. The method of claim 1 wherein said Aloe extract is obtained from any species of Aloe containing aloesin.

5. The method of claim 1 wherein the organic solvent is a water miscible organic solvent selected from the group consisting of an alcohol, acetone and acetonitrile or mixtures thereof.

6. The method of claim 5 wherein said alcohol is selected from the group consisting of methanol, ethanol and isopropanol.

7. The method of claim 5 wherein said solvent is an aqueous solution of between 0% and 100% v/v alcohol in $H_2O$.

8. The method of claim 5 wherein said solvent is an aqueous solution between 25%–30% v/v alcohol in $H_2O$.

9. The method of claim 5 wherein said solvent is an aqueous solution of 30% v/v alcohol in water.

10. The method of claim 5 wherein said solvent is a mixture of 90% acetonitrile and 10% etol (v/v).

11. The method of claim 1 wherein said volume is reduced using ultrafiltration or reverse osmosis.

12. The method of claim 1 wherein said volume is reduced to a concentration of approximately 126 mg/mL of aloesin or greater.

13. A method for the purification of aloesin comprising the steps of:
   a) concentrating the volume of an aloe extract containing at least 45% aloesin to dryness;
   b) lyophilizing said concentrated product;
   c) dissolving said lyophilized product in an organic solvent or aqueous solution thereof;
   d) allowing said aloesin to crystallize from said solution; and
   c) isolating said crystallized aloesin.

14. The method of claim 13 further comprising the step of cooling said solution of aloesin during step d).

15. The method of claim 14 wherein said solution is cooled to about 4° C.

16. The method of claim 13 wherein said Aloe extract is obtained from any species of Aloe containing aloesin.

17. The method of claim 13 wherein the solvent is a water miscible organic solvent selected from the group consisting of an alcohol, acetone and acetonitrile or mixtures thereof.

18. The method of claim 17 wherein said alcohol is selected from the group consisting of methanol, ethanol and isopropanol.

19. The method of claim 17 wherein said solvent is an aqueous solution of between 0% and 100% v/v alcohol in $H_2O$.

20. The method of claim 17 wherein said solvent is an aqueous solution between 25%–30% v/v alcohol in $H_2O$.

21. The method of claim 17 wherein said solvent is an aqueous solution of 30% alcohol v/v in water.

22. The method of claim 17 wherein said solvent is a mixture of 90% acetonitile and 10% ethanol (v/v).

23. The method of claim 13 wherein said volume is reduced using ultrafiltration or reverse osmosis.

24. The method of claim 13 wherein said volume is reduced to a concentration of approximately 126 mg/mL of aloesin or greater.

* * * * *